United States Patent
Lee et al.

(10) Patent No.: US 12,275,972 B2
(45) Date of Patent: Apr. 15, 2025

(54) MICROORGANISM PRODUCING PURINE NUCLEOTIDE AND METHOD OF PRODUCING PURINE NUCLEOTIDE USING THE SAME

(71) Applicant: CJ CHEILJEDANG CORPORATION, Seoul (KR)

(72) Inventors: Ji Hyun Lee, Seoul (KR); Sojung Park, Seoul (KR); Hee Su Kwon, Seoul (KR); Dae Young Kim, Seoul (KR); Ji Hye Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 61 days.

(21) Appl. No.: 17/296,375

(22) PCT Filed: Feb. 19, 2021

(86) PCT No.: PCT/KR2021/002150
§ 371 (c)(1),
(2) Date: May 24, 2021

(87) PCT Pub. No.: WO2021/167414
PCT Pub. Date: Aug. 26, 2021

(65) Prior Publication Data
US 2022/0380821 A1 Dec. 1, 2022

(30) Foreign Application Priority Data

Feb. 21, 2020 (KR) .................. 10-2020-0021383

(51) Int. Cl.
*C12P 19/32* (2006.01)
*C07K 14/34* (2006.01)
*C12N 15/77* (2006.01)

(52) U.S. Cl.
CPC .............. *C12P 19/32* (2013.01); *C07K 14/34* (2013.01); *C12N 15/77* (2013.01); *C12N 2800/101* (2013.01)

(58) Field of Classification Search
CPC ...................................................... C12P 19/32
See application file for complete search history.

(56) References Cited

U.S. PATENT DOCUMENTS

2015/0307907 A1* 10/2015 Hirano ................. C12P 13/04
435/252.32

FOREIGN PATENT DOCUMENTS

| | | |
|---|---|---|
| JP | 3503705 B2 | 3/2004 |
| JP | 2012-522503 A | 9/2012 |
| JP | 2013-521826 A | 6/2013 |
| JP | 2015-29474 A | 2/2015 |
| KR | 10-2015-0099809 A | 9/2015 |
| KR | 10-1950141 B1 | 2/2019 |
| KR | 10-1956510 B1 | 3/2019 |
| KR | 10-2185850 B1 | 12/2020 |
| WO | 03/008607 A2 | 1/2003 |
| WO | 2015/050276 A1 | 4/2015 |
| WO | 2019/147078 A1 | 8/2019 |

OTHER PUBLICATIONS

Schulte et al., "Identification of the cAMP phosphodiesterase CpdA as novel key player in cAMP-dependent regulation in Corynebacterium glutamicum", Molecular Microbiology, 2017, 103(3), 534-552.*
KEGG Purine metabolism—Corynebacterium glutamicum ATCC 13032 (Bielefeld)—Retrieved from < https://www.genome.jp/pathway/cgb00230 > on Apr. 24, 2024.*
Corynebacterium stationis ATCC 6872 genome information CP014279.1, deposited Feb. 5, 2016. Retrieved from <https://www.ncbi.nlm.nih.gov/datasets/genome/GCF_001561975/ > on Sep. 10, 2024.*
KEGG Purine Metabolism—Corynebacterium stationis, Retrieved from < https://www.kegg.jp/kegg-bin/show_pathway?csta00230 > on Sep. 10, 2024.*
Aguena et al., "Transcriptional analysis of the pst operon of *Escherichia coli*," Mol Genet Genomics 268:518-524 (2002).
Chan et al., "PstB Protein of the Phosphate-Specific Transport System of *Escherichia coli* Is an ATPase," Journal of Bacteriology 178(13):3974-3977 (1996).
Surin et al., "Phosphate-Specific Transport System of *Escherichia coli*: Nucleotide Sequence and Gene-Polypeptide Relationships," Journal of Bacteriology 161(1):189-198 (1985).
Webb et al., "Mutational Analysis of the *Escherichia coli* Phosphate-specific Transport System, a Member of the Traffic ATPase (or ABC) Family of Membrane Transporters," The Journal of Biological Chemistry 267(34):24661-24668 (1992).
Lindner et al., "NCgl2620 Encodes a Class II Polyphosphate Kinase in *Corynebacterium glutamicum*," Applied and Environmental Microbiology 73(15):5026-5033 (2007).
Ishige et al., "The Phosphate Starvation Stimulon of *Corynebacterium glutamicum* Determined by DNA Microarray Analyses," Journal of Bacteriology 185(15):4519-4529 (2003).
Uniprot A0A0X8VK01, 2 pages (Apr. 13, 2016).
Uniprot A0A241TY98, 1 page (Oct. 25, 2017).

* cited by examiner

*Primary Examiner* — Suzanne M Noakes
(74) *Attorney, Agent, or Firm* — Seed IP Law Group LLP

(57) ABSTRACT

Provided are a microorganism of the genus *Corynebacterium* which produces a purine nucleotide, and a method of producing a purine nucleotide using the microorganism.

5 Claims, No Drawings

Specification includes a Sequence Listing.

SEQUENCE LISTING

```
<160> NUMBER OF SEQ ID NOS: 33

<210> SEQ ID NO 1
<211> LENGTH: 372
<212> TYPE: PRT
<213> ORGANISM: Unknown
<220> FEATURE:
<223> OTHER INFORMATION: PstS

<400> SEQUENCE: 1

Met Ile Arg Asn Phe Lys Arg Ser Ala Ala Ile Ile Gly Ala Val Ala
1               5                   10                  15

Ala Ser Ser Val Ala Leu Val Ala Cys Ser Asp Ser Ala Asp Asp Ser
                20                  25                  30

Ala Asn Gly Gly Glu Ala Ala Ala Glu Leu Pro Gly Gly Tyr Ala Leu
            35                  40                  45

Ser Gly Ala Thr Gly Gly Leu Val Ala Glu Gly Ala Ser Ser Gln Gln
        50                  55                  60

Asn Ala Met Asp Tyr Phe Gly Ala Met Tyr Gln Glu Ala Thr Gly Gly
65                  70                  75                  80

Asp Ala Tyr Leu Glu Tyr Asn Pro Thr Gly Ser Gly Ser Gly Arg Thr
                85                  90                  95

Asn Phe Val Ala Gly Gln Val Val Phe Ala Gly Ser Asp Ser Pro Leu
                100                 105                 110

Glu Glu Asp Gln Val Glu Ala Ala Ala Glu Arg Cys Gly Gly Asn Asp
            115                 120                 125

Ala Trp His Leu Pro Phe Val Ile Gly Pro Val Ala Ile Ala Tyr Asn
        130                 135                 140

Leu Glu Gly Val Glu Glu Ser Ile Asn Leu Ser Thr Glu Thr Leu Gly
145                 150                 155                 160

Lys Ile Phe Ala Gly Asp Ile Thr Lys Trp Asn Asp Asp Ala Ile Ala
                165                 170                 175
```

```
Ser Glu Asn Glu Gly Val Glu Leu Pro Asp Thr Asp Ile Ser Val Val
            180                 185                 190

Tyr Arg Ser Asp Glu Ser Gly Thr Ser Asp Asn Phe Gln Lys Phe Leu
        195                 200                 205

Ser Ala Ser Thr Gly Asp Trp Glu Gly Glu Thr Asn Phe Pro Thr
210                 215                 220

Ala Val Gly Glu Gly Ala Asn Gly Ser Ser Gly Val Ala Thr Gln Val
225                 230                 235                 240

Gln Gln Ile Asn Gly Gly Ile Thr Tyr Val Glu His Ser His Ala Ala
                245                 250                 255

Asp Ser Gly Leu Asp Ile Ala Asn Ile Asp Phe Gly Asn Gly Pro Thr
            260                 265                 270

Glu Leu Asn Glu Glu Ser Val Gly Ala Ala Leu Glu Ala Met Glu Phe
        275                 280                 285

Thr Thr Glu Gly Asn Asp Met Val Val Asp Ser Asp Ala Leu Phe Ala
    290                 295                 300

Ser Asp Ala Gly Tyr Pro Leu Ile Leu Thr Thr Tyr Glu Ile Val Cys
305                 310                 315                 320

Ser Gly Gly Tyr Ser Glu Asp Glu Ala Asn Leu Val Lys Asp Phe Leu
                325                 330                 335

Met Thr Ala Leu Ala Tyr Gln Asp Glu Gly Leu Ser Glu Ala Gly His
            340                 345                 350

Ile Pro Val Thr Gly Gly His Tyr Asp Arg Leu Val Glu Ala Val Glu
        355                 360                 365

Ala Ile Asn Ser
    370

<210> SEQ ID NO 2
<211> LENGTH: 1119
<212> TYPE: DNA
<213> ORGANISM: Unknown
<220> FEATURE:
<223> OTHER INFORMATION: pstS

<400> SEQUENCE: 2
gtgattcgca actttaagcg ctccgctgcc atcatcggtg ccgtcgcagc ttcctctgtc      60
gcactggtag cttgctctga ttccgcagat gattctgcaa acggcggcga agcagcagca     120
gagctgcctg gcggttacgc gctctctggc gcaaccggcg gcctagttgc tgaaggtgcg     180
tcctctcagc aaaacgccat ggactacttc ggtgcgatgt accaggaagc cactggtggc     240
gacgcttact ggagtacaa cccaactggt tccggttccg gccgtaccaa cttcgtcgct     300
ggccaggtag tctttgcagg ttctgactcc cctctggagg aggaccaggt agaggcagct     360
gcagagcgct gtggcggcaa cgatgcatgg cacctgccat tcgttattgg cccagttgca     420
atcgcctaca accttgaggg cgttgaagag tccatcaacc tgagcaccga aaccctgggc     480
aagattttcg ctggcgacat caccaagtgg aacgatgacg caatcgcttc tgagaacgaa     540
ggcgttgaac tgccagatac tgacatctcc gtggtttacc gttccgacga gtccggtacc     600
tcggacaact tccagaagtt cctgagcgct tccaccggtg actgggaagg cgaaggcacc     660
aacttcccaa ccgcagttgg tgaaggcgca acggttcttc cggtgttgc tacccaggtt     720 cagcagatca acggtggcat cacctacgtc gagcactctc acgcagcaga ctccggtctg     780
gacattgcga acatcgactt cggcaacggc ccaaccgagc tgaacgaaga gtccgtgggt     840
gcggcacttg aggctatgga gttcaccacc gagggcaacg acatggttgt cgactccgat     900
```

```
gcactcttcg cttccgatgc aggttaccca ctcatcctga ccacttacga gattgtttgc    960
tccggtggat acagcgaaga tgaggcaaac ttggtcaagg acttcctgat gaccgcactg   1020
gcttaccagg atgagggcct gtctgaggct ggccacattc agtaaccgg tggccactat   1080 gaccgcctcg ttgaggctgt tgaagcaatc aacagctaa                         1119
```

<210> SEQ ID NO 3
<211> LENGTH: 356
<212> TYPE: PRT
<213> ORGANISM: Unknown
<220> FEATURE:
<223> OTHER INFORMATION: PstC

<400> SEQUENCE: 3

```
Met Ala Asp Tyr Asn Ser Thr Ser Gly Asp His Val Lys Leu Glu Asp
1               5                   10                  15

Asn Arg Thr Val Asp Thr His Pro Val Thr Val Asn Ser Ser Gly Ala
            20                  25                  30

Ala Ala Pro Ala Gly Val Asp Asn Gly Ala Thr Pro Lys Ala Val Arg
        35                  40                  45

Arg Ile Gly Asp Arg Val Phe Glu Thr Leu Ser Thr Ala Ser Ala Thr
    50                  55                  60

Leu Ile Thr Val Phe Ile Ala Ala Ile Gly Ile Phe Leu Val Leu Arg
65                  70                  75                  80

Ala Ile Pro Ala Leu Asn Arg Asn Ala Asn Gly Phe Leu Gly Phe Phe
                85                  90                  95

Thr Tyr Thr Asp Thr Trp Asn Thr Ser Asp Val Glu Asn Met Tyr Phe
            100                 105                 110

Gly Ile Pro Asn Leu Phe Ala Ala Thr Val Met Met Ser Val Leu Ala
        115                 120                 125

Leu Ile Ile Ala Met Pro Ile Ala Leu Gly Val Ala Ile Phe Leu Ser
    130                 135                 140

Asn Tyr Ala Pro Lys Ser Ile Val Lys Pro Met Gly Tyr Leu Val Asp
145                 150                 155                 160

Met Leu Ala Ala Val Pro Ser Ile Val Tyr Gly Leu Trp Gly Trp Leu
                165                 170                 175

Val Leu Gly Pro Phe Leu Ser Gly Phe Tyr Lys Trp Ile Glu Ser Trp
            180                 185                 190

Gly Ser Gly Phe Phe Leu Phe Ala Thr Tyr Ser Asn Ser Pro Ser Phe
        195                 200                 205

Glu Thr Gly Arg Asn Leu Phe Thr Gly Gly Ile Val Leu Ala Ile Met
    210                 215                 220

Ile Leu Pro Ile Ile Ala Ala Thr Thr Arg Glu Ile Phe Val Gln Thr
225                 230                 235                 240

Pro Lys Gly Gln Val Glu Ser Ala Leu Ala Leu Gly Ala Thr Arg Trp
                245                 250                 255

Glu Val Val Arg Met Thr Val Leu Pro Phe Gly Met Ser Gly Tyr Ile
            260                 265                 270

Ser Gly Ser Met Leu Gly Leu Gly Arg Ala Leu Gly Glu Thr Met Ala
        275                 280                 285

Leu Tyr Met Val Val Ser Pro Ser Thr Ala Phe Arg Gly Ser Leu Phe
    290                 295                 300

Asp Gly Gly Thr Thr Phe Ala Thr Ala Ile Ala Asn Ala Ala Pro Glu
305                 310                 315                 320
```

```
Phe Asn Asn Asp Ile Lys Ala Gly Ala Tyr Ile Ala Ala Gly Leu Val
            325                 330                 335

Leu Phe Leu Leu Thr Phe Val Val Asn Ala Ile Ala Arg Ser Ile Val
        340                 345                 350

Ala Gly Lys Lys
        355

<210> SEQ ID NO 4
<211> LENGTH: 1071
<212> TYPE: DNA
<213> ORGANISM: Unknown
<220> FEATURE:
<223> OTHER INFORMATION: pstC

<400> SEQUENCE: 4
gtggctgact acaactcgac ctcgggcgac cacgtcaaac tggaagataa ccgaaccgtt      60
gatacccatc cggtgaccgt aaactccagc ggtgccgcgg cacctgcagg tgtagataac     120
ggtgccactc cgaaagccgt tcgtcgcatc ggcgaccgcg ttttcgaaac gctatcccact    180 gcatccgcaa cactgattac ggtattcatt gccgccatcg gtatcttcct tgtcctccgt    240
gcaattcctg cacttaaccg aaacgccaac ggattcctag gattctttac gtacaccgat    300
acgtggaata cctccgatgt tgagaacatg tacttcggca ttccgaaccct gttcgcagca   360 accgtcatga tgtcagtctt ggcgttgatc atcgctatgc caattgcttt gggcgttgcg    420
atcttcttgt ccaactacgc accaaagtcc atcgttaagc caatgggcta cttggtcgac    480
atgctagctg cagttccttc catcgtttac ggcctgtggg gctggctggt gcttggccca    540
ttcctatctg gcttctacaa gtggattgaa agctggggga gcggcttctt cctgtttgcg    600
acctacagca acagcccatc gtttgaaacc ggccgtaacc tgtttaccgg tggcattgtt    660
ctagcaatca tgattttgcc aatcattgcc gcaaccacac gcgaaatctt cgtgcagacg    720
cctaaaggcc aggtcgaatc cgcattggct ctcggcgcta cccgctggga agttgtacgc    780
atgaccgtgc tgcctttcgg tatgtccggc tacatctccg gttcgatgct cggcttgggc    840
cgcgcccttg gtgaaaccat ggcgctatac atggtggttt ccccatcgac cgcattccgc    900
ggttcgttat ttgacggtgg tacaacattt gcaaccgcaa ttgcgaacgc ggcaccggaa    960
tttaataacg acatcaaggc aggcgcttat attgctgccg gcctagtcct gttcctcttg   1020
accttcgtgg tcaacgcgat tgctcgctcg attgttgcgg gcaagaaata g            1071

<210> SEQ ID NO 5
<211> LENGTH: 305
<212> TYPE: PRT
<213> ORGANISM: Unknown
<220> FEATURE:
<223> OTHER INFORMATION: PstA

<400> SEQUENCE: 5

Met Thr Asn Ile Thr Ala Pro Ala Gln Thr Gly Val Gly Lys Thr Ser
1               5                   10                  15

Ala Phe Leu Gln Ile Ser Ala Arg Arg Lys Ala Thr Asp Asn Ile Ala
            20                  25                  30

Lys Tyr Leu Ile Tyr Phe Cys Met Gly Leu Ala Val Ile Pro Leu Ile
        35                  40                  45

Leu Val Leu Trp Glu Leu Ile Ser Lys Gly Leu Pro Pro Val Leu Asn
    50                  55                  60

Ala Glu Trp Trp Thr Asp Asp Met Leu Gly Thr Arg Tyr Ala Gln Glu
65                  70                  75                  80
```

Gly Gly Gly Ala Ile His Ala Ile Ile Gly Thr Leu Val Gln Ser Val
            85                  90                  95

Leu Ala Ser Ile Ile Ala Ile Pro Ile Gly Ile Phe Thr Ala Ile Tyr
            100                 105                 110

Leu Val Glu Tyr Ser Arg Gly Gly Trp Leu Gly Arg Thr Thr Thr Phe
            115                 120                 125

Met Val Asp Ile Leu Ser Gly Val Pro Ser Ile Val Ala Ala Leu Phe
130                 135                 140

Val Tyr Ala Ala Trp Ile Thr Val Leu Gly Phe Asp Arg Ser Gly Leu
145                 150                 155                 160

Ala Val Ala Trp Ser Leu Leu Leu Met Ile Pro Ile Val Val Arg
            165                 170                 175

Asn Thr Glu Glu Met Leu Arg Val Val Pro Met Asp Leu Arg Glu Ala
            180                 185                 190

Ala Tyr Ala Leu Gly Val Pro Lys Trp Lys Thr Ile Ala Arg Ile Val
            195                 200                 205

Leu Pro Thr Ala Leu Ser Gly Ile Ala Thr Gly Ile Met Leu Ala Ile
            210                 215                 220

Ala Arg Ile Met Gly Glu Ser Ala Pro Val Leu Ile Leu Val Gly Thr
225                 230                 235                 240

Thr Pro Ala Leu Lys Trp Asp Pro Thr Gly Gly Pro Met Ser Ser Leu
            245                 250                 255

Pro Leu Met Met Leu Asp Met Phe Lys Ala Gly Leu Asn Pro Asn Val
            260                 265                 270

Leu Asp Lys Met Trp Gly Ala Ala Phe Thr Leu Val Leu Ile Ile Ala
            275                 280                 285

Ile Leu Asn Ile Gly Ala Arg Val Ile Ser Ala Lys Phe Ser Ile Lys
            290                 295                 300

Gln
305

<210> SEQ ID NO 6
<211> LENGTH: 918
<212> TYPE: DNA
<213> ORGANISM: Unknown
<220> FEATURE:
<223> OTHER INFORMATION: pstA

<400> SEQUENCE: 6

```
atgactaaca ttacagctcc tgcacaaacc ggagtcggta aaacctccgc gttcttgcaa    60
atctcggctc gccgcaaggc caccgataat atcgctaagt atctcatcta cttctgcatg   120
ggcttagcag taattccttt gattctcgtt ctgtgggaac tgatttctaa gggccttcca   180
ccagtgctca acgctgaatg gtggaccgat gacatgctgg gtacccgcta cgcccaagaa   240
ggaggcggcg cgatccatgc gattatcggt accttggtgc agtcggttct agcatctatc   300
atcgctatcc ctatcggtat cttcaccgca atctacttgg ttgagtactc ccgtggcggc   360
tggctcggac gcaccacaac cttcatggtg gatatcttgt ccggtgtgcc ttcgatcgtt   420
gcagcactgt tcgtctacgc ggcctggatt acggtcctag gtttcgaccg ctccggcttg   480
gccgtggctt ggtccctgtt gctgttgatg attccaattg tggttcgcaa caccgaagaa   540
atgctgcgcg ttgttccaat ggacttgcgc gaggctgcct acgctcttgg cgttccaaag   600
tggaagacta tcgcgcgcat tgttcttcca actgcattgt ccggtattgc aaccggcatc   660
atgctggcga ttgcccgcat catgggtgag tctgcaccag ttctgattct ggttggtacc   720
```

```
accccggcgc tgaagtggga ccccaccggt ggcccaatgt cttccttgcc gttgatgatg    780
ctcgatatgt tcaaggccgg tttgaacccg aatgttcttg acaagatgtg gggcgcagca    840
ttcacgctgg ttctgatcat cgcaatttta aatattggtg ctcgcgtaat tccgcgaaa     900 ttctccatca aacagtag                                                  918
```

```
<210> SEQ ID NO 7
<211> LENGTH: 257
<212> TYPE: PRT
<213> ORGANISM: Unknown
<220> FEATURE:
<223> OTHER INFORMATION: PstB

<400> SEQUENCE: 7
```

Met Ser Lys Leu Glu Leu Asn Asp Val Asp Ile Phe Tyr Gly Asp Phe
1               5                   10                  15

His Ala Val Gln Asn Val Asn Met His Ile Pro Ala Gln Ala Val Thr
            20                  25                  30

Ala Phe Ile Gly Pro Ser Gly Cys Gly Lys Ser Thr Val Leu Arg Ser
        35                  40                  45

Ile Asn Arg Met His Glu Val Ile Pro Gly Ala Tyr Val Lys Gly Glu
    50                  55                  60

Ile Leu Leu Asp Gly Glu Asn Ile Tyr Gly Ser Lys Ile Asp Pro Val
65                  70                  75                  80

Ser Val Arg Asn Thr Ile Gly Met Val Phe Gln Lys Ala Asn Pro Phe
                85                  90                  95

Pro Thr Met Ser Ile Glu Asp Asn Val Ala Gly Leu Lys Leu Ser
            100                 105                 110

Gly Val Lys Asp Lys Lys Leu Lys Glu Val Ala Glu Lys Ser Leu
        115                 120                 125

Arg Gly Ala Asn Leu Trp Asp Glu Val Lys Asp Arg Leu Asp Lys Pro
130                 135                 140

Gly Gly Gly Leu Ser Gly Gly Gln Gln Gln Arg Leu Cys Ile Ala Arg
145                 150                 155                 160

Ala Ile Ala Val Glu Pro Glu Val Leu Leu Met Asp Glu Pro Cys Ser
                165                 170                 175

Ala Leu Asp Pro Ile Ser Thr Leu Ala Val Glu Asp Leu Ile His Glu
            180                 185                 190

Leu Lys Glu Asn Phe Thr Ile Val Ile Val Thr His Asn Met Gln Gln
        195                 200                 205

Ala Ala Arg Val Ser Asp Lys Thr Gly Phe Phe Ser Leu Glu Ala Thr
    210                 215                 220

Gly Arg Pro Gly His Leu Val Glu Phe Asn Glu Thr Lys Lys Ile Phe
225                 230                 235                 240

Glu Asn Pro Asp Lys Lys Glu Thr Glu Asp Tyr Ile Ser Gly Arg Phe
                245                 250                 255

Gly

```
<210> SEQ ID NO 8
<211> LENGTH: 774
<212> TYPE: DNA
<213> ORGANISM: Unknown
<220> FEATURE:
<223> OTHER INFORMATION: pstB

<400> SEQUENCE: 8
```

```
atgtcaaagc tcgaactcaa tgacgtggac atcttctacg gtgatttcca cgctgtgcaa      60
aatgtcaata tgcacatccc ggctcaggca gtgaccgcgt tcattgggcc atccggctgt     120
ggtaagtcca cagttctgcg cagtatcaac cgcatgcacg aagttatccc tggcgcatat     180
gtcaagggtg aaatcctgct cgacggtgaa acatctacg gctcaaagat tgacccagtc     240
tccgtacgca acaccatcgg catggtcttc cagaaagcta atccatttcc aaccatgtcc     300
atcgaggaca acgtggtggc gggcctgaag ctgtccggcg tcaaggacaa gaagaagctc     360
aaggaagtag ctgagaagtc tcttcgcggc gcaaacctgt gggatgaggt caaggaccgt     420
ctggataagc caggcggcgg cctctccggt ggtcagcagc agcgtctgtg catcgctcgc     480
gcgatcgctg tggagccaga agttctgctc atggatgagc catgctcggc actgacccca     540
atttcgaccc ttgctgtgga agatttgatc cacgagctga aggaaaactt caccatcgtg     600
atcgttaccc acaacatgca gcaggctgca cgtgtatccg ataagactgg tttcttctcc     660
ttggaagcaa ctggccgccc tggacacctt gtggaattca acgagaccaa gaagatcttc     720
gaaaacccag ataagaagga aaccgaagac tacatctccg ccgcttcgg ctaa            774

<210> SEQ ID NO 9
<211> LENGTH: 30
<212> TYPE: DNA
<213> ORGANISM: Artificial Sequence
<220> FEATURE:
<223> OTHER INFORMATION: pstS(ATG)-A-F

<400> SEQUENCE: 9
gggtctagac cacaaacaga attaatggta                                       30

<210> SEQ ID NO 10
<211> LENGTH: 27
<212> TYPE: DNA
<213> ORGANISM: Artificial Sequence
<220> FEATURE:
<223> OTHER INFORMATION: pstS(ATG)-A-R

<400> SEQUENCE: 10
gcttaaagtt gcgaatcatg gggaaac                                          27

<210> SEQ ID NO 11
<211> LENGTH: 27
<212> TYPE: DNA
<213> ORGANISM: Artificial Sequence
<220> FEATURE:
<223> OTHER INFORMATION: pstS(ATG)-B-F

<400> SEQUENCE: 11
ccggaaaggt ttccccatga ttcgcaa                                          27

<210> SEQ ID NO 12
<211> LENGTH: 30
<212> TYPE: DNA
<213> ORGANISM: Artificial Sequence
<220> FEATURE:
<223> OTHER INFORMATION: pstS(ATG)-B-R

<400> SEQUENCE: 12
gggtctagag acgtaggtga tgccaccgtt                                       30

<210> SEQ ID NO 13
<211> LENGTH: 14
<212> TYPE: DNA
<213> ORGANISM: Artificial Sequence
```

```
<220> FEATURE:
<223> OTHER INFORMATION: pstS(ATG)-mismatch-wt-F

<400> SEQUENCE: 13
gaaaggtttc cccg                                                         14

<210> SEQ ID NO 14
<211> LENGTH: 14
<212> TYPE: DNA
<213> ORGANISM: Artificial Sequence
<220> FEATURE:
<223> OTHER INFORMATION: pstS(ATG)-mismatch-mut-F

<400> SEQUENCE: 14
gaaaggtttc ccca                                                         14

<210> SEQ ID NO 15
<211> LENGTH: 30
<212> TYPE: DNA
<213> ORGANISM: Artificial Sequence
<220> FEATURE:
<223> OTHER INFORMATION: pstC(ATG)-A-F

<400> SEQUENCE: 15
gggtctagac atcaacctga gcaccgaaac                                         30

<210> SEQ ID NO 16
<211> LENGTH: 27
<212> TYPE: DNA
<213> ORGANISM: Artificial Sequence
<220> FEATURE:
<223> OTHER INFORMATION: pstC(ATG)-A-R

<400> SEQUENCE: 16
tcaggagtgt cgtaaacata ccataca                                            27

<210> SEQ ID NO 17
<211> LENGTH: 27
<212> TYPE: DNA
<213> ORGANISM: Artificial Sequence
<220> FEATURE:
<223> OTHER INFORMATION: pstC(ATG)-B-F

<400> SEQUENCE: 17
cgctggcttg tatggtatgt ttacgac                                            27

<210> SEQ ID NO 18
<211> LENGTH: 30
<212> TYPE: DNA
<213> ORGANISM: Artificial Sequence
<220> FEATURE:
<223> OTHER INFORMATION: pstC(ATG)-B-R

<400> SEQUENCE: 18
gggtctagaa ccggtaaaca ggttacggcc                                         30

<210> SEQ ID NO 19
<211> LENGTH: 14
<212> TYPE: DNA
<213> ORGANISM: Artificial Sequence
<220> FEATURE:
<223> OTHER INFORMATION: pstC(ATG)-mismatch-wt-F

<400> SEQUENCE: 19
tggcttgtat ggtg                                                         14
```

<210> SEQ ID NO 20
<211> LENGTH: 14
<212> TYPE: DNA
<213> ORGANISM: Artificial Sequence
<220> FEATURE:
<223> OTHER INFORMATION: pstC(ATG)-mismatch-mut-F

<400> SEQUENCE: 20
tggcttgtat ggta                                                      14

<210> SEQ ID NO 21
<211> LENGTH: 33
<212> TYPE: DNA
<213> ORGANISM: Artificial Sequence
<220> FEATURE:
<223> OTHER INFORMATION: pstSCAB-Xba-F

<400> SEQUENCE: 21
tgctctagag aagtggcacg atgaagtatc gcc                                 33

<210> SEQ ID NO 22
<211> LENGTH: 34
<212> TYPE: DNA
<213> ORGANISM: Artificial Sequence
<220> FEATURE:
<223> OTHER INFORMATION: pstSCAB XbaI-R

<400> SEQUENCE: 22
tgctctagag cagtcgatat tgcgctgcta tcac                                34

<210> SEQ ID NO 23
<211> LENGTH: 34
<212> TYPE: DNA
<213> ORGANISM: Artificial Sequence
<220> FEATURE:
<223> OTHER INFORMATION: pstSCAB SpeI-R

<400> SEQUENCE: 23
acgactagtg cagtcgatat tgcgctgcta tcac                                34

<210> SEQ ID NO 24
<211> LENGTH: 24
<212> TYPE: DNA
<213> ORGANISM: Artificial Sequence
<220> FEATURE:
<223> OTHER INFORMATION: pstSCAB-2copy-check-F

<400> SEQUENCE: 24
caccatcgtg atcgttaccc acaa                                           24

<210> SEQ ID NO 25
<211> LENGTH: 25
<212> TYPE: DNA
<213> ORGANISM: Artificial Sequence
<220> FEATURE:
<223> OTHER INFORMATION: pstSCAB-2copy-check-R

<400> SEQUENCE: 25
gaatcatctg cggaatcaga gcaag                                          25

<210> SEQ ID NO 26
<211> LENGTH: 28
<212> TYPE: DNA
<213> ORGANISM: Artificial Sequence
<220> FEATURE:
<223> OTHER INFORMATION: PstSpro-A-F

```
<400> SEQUENCE: 26
tgctctagag aagcagttgc cgcaagcg                                    28

<210> SEQ ID NO 27
<211> LENGTH: 45
<212> TYPE: DNA
<213> ORGANISM: Artificial Sequence
<220> FEATURE:
<223> OTHER INFORMATION: PstS-pro-A-R

<400> SEQUENCE: 27
catatggaat tccggatccg gggaaacctt tccggttaat ttcag                 45

<210> SEQ ID NO 28
<211> LENGTH: 40
<212> TYPE: DNA
<213> ORGANISM: Artificial Sequence
<220> FEATURE:
<223> OTHER INFORMATION: PstSpro-B-F

<400> SEQUENCE: 28
ggatccggaa ttccatatga ttcgcaactt aagcgctcc                        40

<210> SEQ ID NO 29
<211> LENGTH: 29
<212> TYPE: DNA
<213> ORGANISM: Artificial Sequence
<220> FEATURE:
<223> OTHER INFORMATION: PstSpro-B-R

<400> SEQUENCE: 29
tgctctagac agacaggccc tcatcctgg                                   29

<210> SEQ ID NO 30
<211> LENGTH: 34
<212> TYPE: DNA
<213> ORGANISM: Artificial Sequence
<220> FEATURE:
<223> OTHER INFORMATION: CJ7pro-F

<400> SEQUENCE: 30
cgcggatcct tccttcaggc taatctttc cggg                              34

<210> SEQ ID NO 31
<211> LENGTH: 40
<212> TYPE: DNA
<213> ORGANISM: Artificial Sequence
<220> FEATURE:
<223> OTHER INFORMATION: CJ7pro-R

<400> SEQUENCE: 31
ggaattccat atgcatatgt gtttccttc gttgggtacg                        40

<210> SEQ ID NO 32
<211> LENGTH: 25
<212> TYPE: DNA
<213> ORGANISM: Artificial Sequence
<220> FEATURE:
<223> OTHER INFORMATION: CJ7pro-check-F

<400> SEQUENCE: 32
ctacgacctc agcgtgattg gtttg                                       25

<210> SEQ ID NO 33
```

```
<211> LENGTH: 25
<212> TYPE: DNA
<213> ORGANISM: Artificial Sequence
<220> FEATURE:
<223> OTHER INFORMATION: PstS-check-R

<400> SEQUENCE: 33
caggaagtcc ttgaccaagt ttgcc                                    25
```

MICROORGANISM PRODUCING PURINE NUCLEOTIDE AND METHOD OF PRODUCING PURINE NUCLEOTIDE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_474USPC_SEQUENCE_LISTING_V2.txt. The text file is 21.4 KB, was created on Feb. 20, 2024, and is being submitted electronically via Patent Center.

BACKGROUND OF THE INVENTION

1. Field of the Invention

The present disclosure relates to a microorganism of the genus *Corynebacterium* which produces a purine nucleotide, and a method of producing a purine nucleotide using the microorganism.

2. Description of the Related Art

Purine nucleotides, for example, 5'-inosine monophosphate (hereinafter referred to as IMP), 5'-xanthosine monophosphate (hereinafter referred to as XMP), and 5'-guanosine monophosphate (hereinafter referred to as GMP), which are intermediates of the nucleic acid biosynthetic metabolic system, have an important physiological role in the body, and are widely used in foods, pharmaceuticals, etc. Specifically, IMP itself is known to impart a beef flavor, and GMP, which is derived from XMP, is known to impart a mushroom flavor. Both materials are known to enhance the taste intensity of monosodium glutamate (MSG), and thus have attracted much attention as a flavor-enriched nucleic acid-based seasoning.

Phosphate, which is a component of purine nucleotides, provides energy necessary for microbial growth, and is essential for the biosynthesis of phospholipids of cell membranes, nucleic acids, and proteins. It also has a major role in the cellular signaling process.

Phosphate is mainly absorbed into cells in the form of inorganic orthophosphate (hereinafter referred to as $P_i$). $P_i$ influx into microorganisms depends on the function of importers present in the cell membrane. The previously known $P_i$ importers include a Pst system, which is a high-affinity $P_i$ importer system, and of which expression is regulated by recognizing the extracellular $P_i$ concentration; a Pit system, which expresses regardless of the $P_i$ concentration and introduces $P_i$ in a mixed form with metal ions; and an antiporter transport system, which introduces glycerol-3-phosphate and glucose-6-phosphate in the form of organophosphate, etc.

Several types of methods used in the amino acid production by controlling the Pst system among the $P_i$ importer systems have been reported (PCT Patent Nos. WO 2015-050276 and WO 2003-008607), but the influence of the Pst system differs depending on microorganisms to be used or desired products.

The present inventors found that the influx of the key component phosphate is important during production of purine nucleotides through microbial fermentation. Accordingly, the present inventors demonstrated that production of purine nucleotides may be improved by controlling an expression level of the phosphate importer in a microorganism, thereby completing the present disclosure.

SUMMARY OF THE INVENTION

An object of the present disclosure is to provide a microorganism of the genus *Corynebacterium* producing a purine nucleotide, in which activity of a phosphate importer is enhanced.

Another object of the present disclosure is to provide a method of producing a purine nucleotide, the method including the step of culturing, in a medium, the microorganism of the genus *Corynebacterium* producing the purine nucleotide, in which activity of a phosphate importer is enhanced.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the above objects, an aspect of the present disclosure provides a microorganism of the genus *Corynebacterium* producing a purine nucleotide, in which activity of a phosphate importer is enhanced.

As used herein, the term "phosphate importer" refers to a protein that has a role in intracellular uptake of phosphate. Phosphate is mainly absorbed into cells in the form of inorganic orthophosphate (hereinafter referred to as $P_i$), and is known to depend on the function of the importers present in the cell membrane. Specifically, the previously known Pi importers include a Pst system, a Pit system, and an antiporter transport system, which introduces glycerol-3-phosphate and glucose-6-phosphate in the form of organophosphate, etc., but are not limited thereto.

With respect to the objects of the present disclosure, the phosphate importer may be the Pst system, but is not limited thereto.

As used herein, the term "Pst system" refers to a phosphate adenosine triphosphate-binding cassette transport system, which is a phosphate importer, i.e., $P_i$ importer, and has high affinity for $P_i$. The Pst system is known to be expressed by a pst operon consisting of a phosphate binding protein (hereinafter referred to as PstS), an inner membrane subunit of the phosphate adenosine triphosphate-binding cassette transporter (phosphate ATP-binding cassette transporter; hereinafter referred to as PstC), a permease protein of the phosphate adenosine triphosphate-binding cassette transporter (phosphate ATP-binding cassette transporter; hereinafter referred to as PstA), and an adenosine triphosphate-binding protein (ATP-binding protein) of the phosphate adenosine triphosphate-binding cassette transporter (phosphate ABC transporter; hereinafter, referred to as PstB; Aguena et al., 2002). Specifically, it is known that PstS has a role in intracellular uptake of $P_i$ by recognizing extracellular $P_i$ concentrations (Surin et al., 2002), PstC and PstA, which are transmembrane proteins, are used as paths through which $P_i$ moves into cells, and PstB binds to adenosine triphosphate to obtain energy for $P_i$ uptake (Webb et al., 1992; Chan and Torriani, 1996). It has been reported that the pst operon remains suppressed when extracellular concentrations of $P_i$ are abundant, and the expression thereof is enhanced when the extracellular concentrations of $P_i$ are low at micromolar (μM) levels or less (Surin et al., 1985; Magota K et al., 1982).

In the present disclosure, the PstS may include an amino acid sequence of SEQ ID NO: 1, the PstC may include an amino acid sequence of SEQ ID NO: 3, the PstA may include an amino acid sequence of SEQ ID NO: 5, and the PstB may include an amino acid sequence of SEQ ID NO: 7. Specifically, SEQ ID NO: 1, SEQ ID NO: 3, SEQ ID NO: 5, or SEQ ID NO: 7 may each be a protein sequence having activity of PstS, PstC, PstA, or PstB encoded by pstS, pstC, pstA, or pstB gene. The amino acid sequence of SEQ ID NO: 1, SEQ ID NO: 3, SEQ ID NO: 5, or SEQ ID NO: 7 may be obtained from NCBI GenBank, which is a public database. For example, the amino acid sequence may be derived from *Corynebacterium stationis*, but is not limited thereto, and may include any sequence having the same activity as the above amino acid sequence without limitation. In addition, although the protein having the activity of PstS, PstC, PstA, or PstB of the present disclosure is defined as the protein including the amino acid sequence of SEQ ID NO: 1, SEQ ID NO: 3, SEQ ID NO: 5, or SEQ ID NO: 7, addition of a meaningless sequence upstream or downstream of the amino acid sequence of SEQ ID NO: 1, SEQ ID NO: 3, SEQ ID NO: 5, or SEQ ID NO: 7, a naturally occurring mutation, or a silent mutation therein is not excluded, and it will be apparent to those skilled in the art that as long as a protein has activity identical or corresponding to the activity of the protein including the amino acid sequence of SEQ ID NO: 1, SEQ ID NO: 3, SEQ ID NO: 5, or SEQ ID NO: 7, it may belong to the protein having the activity of PstS, PstC, PstA, or PstB of the present disclosure. Specifically, the protein having the activity of PstS, PstC, PstA, or PstB of the present disclosure may be a protein consisting of the amino acid sequence of SEQ ID NO: 1, SEQ ID NO: 3, SEQ ID NO: 5, or SEQ ID NO: 7 or an amino acid sequence having 80%, 85%, 90%, 95%, 96%, 97%, 98%, or 99% or more homology or identity thereto. It will be also apparent that any protein having an amino acid sequence with deletion, modification, substitution, or addition in part of the sequence may also be included within the scope of the protein of the present disclosure, as long as the amino acid sequence has such homology or identity and exhibits efficacy corresponding to that of the protein.

In other words, although described as "a protein or polypeptide having an amino acid sequence of a specific SEQ ID NO" or "a protein or polypeptide including an amino acid sequence of a specific SEQ ID NO" in the present disclosure, it is obvious that any protein having an amino acid sequence with deletion, modification, substitution, or addition in part of the sequence may also be used in the present disclosure, as long as the protein may have an activity identical or corresponding to that of the polypeptide consisting of the amino acid sequence of the corresponding SEQ ID NO. For example, it is obvious that any polypeptide may belong to the "polypeptide consisting of the amino acid sequence of SEQ ID NO: 1", as long as it has an activity identical or corresponding to that of the "polypeptide consisting of the amino acid sequence of SEQ ID NO: 1".

In the present disclosure, the amino acid sequence of SEQ ID NO: 1, SEQ ID NO: 3, SEQ ID NO: 5, or SEQ ID NO: 7 may be, for example, encoded by a polynucleotide including a nucleotide sequence of SEQ ID NO: 2, SEQ ID NO: 4, SEQ ID NO: 6, or SEQ ID NO: 8, respectively.

As used herein, the term "polynucleotide", which refers to a long-chain polymer of nucleotides formed by linking nucleotide monomers via covalent bonds, refers to a DNA or RNA strand having a predetermined length or more. In the present disclosure, the polynucleotide may encode the polypeptide exhibiting the activity of PstS, PstC, PstA, or PstB having the amino acid sequence of SEQ ID NO: 1, SEQ ID NO: 3, SEQ ID NO: 5, or SEQ ID NO: 7, respectively, but is not limited thereto.

The polynucleotide may include any polynucleotide without limitation, as long as it is a polynucleotide encoding the polypeptide having the activity of PstS, PstC, PstA, or PstB according to the present disclosure. In the present disclosure, the gene encoding the amino acid sequence of PstS, PstC, PstA, or PstB may be pstS, pstC, pstA, or pstB gene, respectively, and the gene may be derived from *Corynebacterium stationis*, but is not limited thereto.

Specifically, the polynucleotide encoding the polypeptide having the activity of PstS, PstC, PstA, or PstB may include a nucleotide sequence encoding the amino acid sequence of SEQ ID NO: 1, SEQ ID NO: 3, SEQ ID NO: 5, or SEQ ID NO: 7. The polynucleotide may undergo various modifications in the coding region without changing the amino acid sequence of the polypeptide, due to codon degeneracy or in consideration of the codons preferred in an organism in which the polypeptide is to be expressed. The polynucleotide may include, for example, the nucleotide sequence of SEQ ID NO: 2, SEQ ID NO: 4, SEQ ID NO: 6, or SEQ ID NO: 8, and may include a nucleotide sequence having 80%, specifically 90% or more homology thereto, but is not limited thereto.

Further, a probe which may be prepared from a known gene sequence, for example, any polynucleotide sequence which hybridizes with a sequence complementary to all or a part of the polynucleotide sequence under stringent conditions to encode the amino acid sequence of SEQ ID NO: 1, SEQ ID NO: 3, SEQ ID NO: 5, or SEQ ID NO: 7, may be included without limitation. The "stringent conditions" refer to conditions which allow the specific hybridization between polynucleotides. Such conditions are disclosed in detail in the literature (e.g., J. Sambrook et al., supra). For example, the stringent conditions may include conditions under which genes having high homology or identity, genes having 40% or more, specifically 90% or more, more specifically 95% or more, much more specifically 97% or more, and particularly specifically 99% or more homology or identity hybridize with each other, while genes having homology or identity lower than the above homology or identity do not hybridize with each other; or may include ordinary washing conditions of Southern hybridization, i.e., washing once, specifically twice or three times, at a salt concentration and a temperature corresponding to 60° C., 1×SSC, 0.1% SDS, specifically 60° C., 0.1×SSC, 0.1% SDS, and more specifically 68° C., 0.1×SSC, 0.1% SSD.

Hybridization requires that two polynucleotides have complementary sequences, although mismatches between bases are possible depending on the stringency of the hybridization. The term "complementary" is used to describe a relationship between nucleotide bases that may hybridize with each other. For example, with respect to DNA, adenine is complementary to thymine, and cytosine is complementary to guanine. Therefore, the present disclosure may also include an isolated polynucleotide fragment complementary to the entire sequence as well as a polynucleotide sequence substantially similar thereto.

Specifically, a polynucleotide having homology or identity may be detected using hybridization conditions including a hybridization step at a $T_m$ value of 55° C. under the above-described conditions. Additionally, the $T_m$ value may be 60° C., 63° C., or 65° C., but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art (see Sambrook et al., supra, 9.50-9.51, 11.7-11.8).

As used herein, the term "homology" or "identity" refers to the degree of relatedness between two given amino acid sequences or nucleotide sequences, and may be expressed as a percentage. The terms "homology" and "identity" may often be used interchangeably with each other.

The sequence homology or identity of conserved polynucleotides or polypeptides may be determined by standard alignment algorithms and may be used together with a default gap penalty established by the program being used. Substantially, homologous or identical sequences are generally expected to hybridize to all or at least about 50%, about 60%, about 70%, about 80%, or about 90% or more of the entire length of the sequences under moderate or highly stringent conditions. Polynucleotides that contain degenerate codons instead of codons in the hybridizing polynucleotides may also be considered.

Whether any two polynucleotide or polypeptide sequences have homology, similarity, or identity may be determined by a known computer algorithm such as the "FASTA" program using default parameters as in Pearson et al. (1988) *Proc. Natl. Acad. Sci. USA* 85:2444. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J. et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, homology, similarity, or identity may be determined using BLAST or ClustalW of the National Center for Biotechnology Information.

The homology, similarity, or identity of polynucleotides or polypeptides may be determined by comparing sequence information using, for example, the GAP computer program, such as Needleman et al. (1970), *J Mol Biol.* 48:443, as disclosed in Smith and Waterman, *Adv. Appl. Math* (1981) 2:482. In summary, the GAP program defines this as the value obtained by dividing the number of similarly aligned symbols (i.e., nucleotides or amino acids) by the total number of the symbols in the shorter of the two sequences. Default parameters for the GAP program may include (1) a binary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14:6745, as disclosed in Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have homology, similarity, or identity may be determined by comparing sequences via Southern hybridization experiments under defined stringent conditions, and the appropriate hybridization conditions to be defined may be determined by way of a method within the scope of the present disclosure, which is known to those skilled in the art (e.g., J. Sambrook et al., *Molecular Cloning, A Laboratory Manual*, $2^{nd}$ Edition, Cold Spring Harbor Laboratory press, Cold Spring Harbor, New York, 1989; F. M. Ausubel et al., *Current Protocols in Molecular Biology*, John Wiley & Sons, Inc., New York).

In the present disclosure, enhancement of the activity of the phosphate importer system may be enhancement of activity of proteins encoded by any one or more genes selected from the group consisting of pstS, pstC, pstA, and pstB, but is not limited thereto.

The protein encoded by the pstS gene may include the amino acid sequence of SEQ ID NO: 1, but is not limited thereto.

The protein encoded by the pstC gene may include the amino acid sequence of SEQ ID NO: 3, but is not limited thereto.

The protein encoded by the pstA gene may include the amino acid sequence of SEQ ID NO: 5, but is not limited thereto.

The protein encoded by the pstB gene may include the amino acid sequence of SEQ ID NO: 7, but is not limited thereto.

As used herein, the term "enhancement of protein activity" means that protein activity is increased, as compared with endogenous activity thereof. The "endogenous activity" refers to activity of a particular protein originally possessed by a parent strain or a non-modified microorganism before transformation when the microorganism is transformed by genetic variation due to a natural or artificial factor. The endogenous activity may also be interchangeably used with "activity before modification". The term "increase" in the activity of the protein, as compared with the endogenous activity, means that the activity of the protein is enhanced, as compared with activity of a particular protein originally possessed by a parent strain or a non-modified microorganism before transformation.

The "increase in the activity" may be achieved by introducing a foreign protein or enhancing the activity of an endogenous protein, but it may be specifically achieved by enhancing the activity of the endogenous protein. Whether or not the activity of the protein is enhanced may be confirmed from the activity or expression level of the corresponding protein, or the increase in the amount of a product produced from the corresponding protein.

In the present disclosure, a protein to be a target of the activity enhancement, i.e., a target protein, may be a phosphate importer, specifically the Pst system, and more specifically any one or more selected from the group consisting of PstS, PstC, PstA, and PstB, but is not limited thereto. With respect to the objects of the present disclosure, the phosphate importer to be the target of the activity enhancement may be any one or more selected from the group consisting of i) PstS, ii) PstC, or iii) a combination of PstS and PstC, and may further include PstA or PstB in addition thereto, but is not limited thereto.

Further, in the present disclosure, the product produced from the corresponding protein may be a purine nucleotide, but is not limited thereto.

Various methods well known in the art may be applied to the activity enhancement of the protein, and the methods are not limited, as long as they may enhance the activity of the target protein, as compared with that of the microorganism before modification. The method may be, but is not limited to, a method using genetic engineering or protein engineering.

The method of enhancing the protein activity using the genetic engineering may be, for example, performed by:
1) a method of increasing the intracellular copy number of a gene encoding the protein,
2) a method of replacing an expression regulatory sequence of the gene encoding the protein on the chromosome with a sequence having strong activity,
3) a method of modifying a nucleotide sequence of an initiation codon or 5'-UTR region of the protein,
4) a method of modifying a polynucleotide sequence on the chromosome to enhance the activity of the protein,
5) a method of introducing a foreign polynucleotide having the activity of the protein or a codon-optimized variant polynucleotide of the polynucleotide, or
6) a combination of the methods, but is not limited thereto.

The method of enhancing the protein activity using the protein engineering may be, for example, performed by way of a method of analyzing a tertiary structure of a protein to select the exposed site, and then modifying or chemically modifying the same, but is not limited thereto.

1) The increase in the intracellular copy number of the gene encoding the protein may be performed by way of any method known in the art, for example, by introducing a vector into a host cell, wherein the vector is operably linked to the gene encoding the corresponding protein and may replicate and function, irrespective of the host; or by introducing a vector into a host cell, wherein the vector is operably linked to the gene and may integrate the gene into the chromosome of the host cell, but is not limited thereto.

As used herein, the term "vector" refers to a DNA construct containing a target protein-encoding polynucleotide sequence operably linked to a suitable regulatory sequence so as to be able to express the target protein in a suitable host cell. The expression regulatory sequence may include a promoter capable of initiating transcription, any operator sequence for regulating the transcription, a sequence encoding a suitable mRNA ribosome binding site, and a sequence for regulating termination of transcription and translation. Once transformed into an appropriate host cell, the vector may replicate or function independently of the host genome, or may integrate into genome thereof.

The vector used in the present disclosure is not particularly limited, as long as it may replicate in a host cell. Any vector known in the art may be used. Examples of the vectors commonly used may include natural or recombinant plasmids, cosmids, viruses, and bacteriophages. For example, pWE15, M13, λMBL3, λMBL4, λIXII, λASHII, λAPII, λt10, λt11, Charon4A, Charon21A, etc. may be used as a phage vector or cosmid vector. Vectors based on pDZ, pBR, pUC, pBluescriptII, pGEM, pTZ, pCL, pET, etc. may be used as a plasmid vector. The vector applicable in the present disclosure is not particularly limited, and a known expression vector may be used.

As used herein, the term "transformation" means introduction of a recombinant vector including a polynucleotide encoding a target protein into a host cell in such a way that the protein encoded by the polynucleotide is expressed in the host cell. As long as the transformed polynucleotide may be expressed in the host cell, it may be inserted into and located in the chromosome of the host cell or exist extrachromosomally, or it may be in any of the cases.

Further, the term "operably linked" means a functional linkage between a promoter sequence which initiates and mediates transcription of the polynucleotide encoding the target protein of the present disclosure and the polynucleotide sequence.

2) The method of replacing an expression regulatory sequence of the gene encoding the protein on the chromosome with a sequence having strong activity may be performed by way of any method known in the art, for example, by inducing a variation in the sequence via deletion, insertion, non-conservative or conservative substitution, or any combination thereof so as to further enhance the activity of the expression regulatory sequence; or by replacing the sequence with a nucleotide sequence having a stronger activity. The expression regulatory sequence may include, but is not particularly limited to, a promoter, an operator sequence, a sequence encoding a ribosome-binding site, a sequence for regulating termination of transcription and translation, etc. Specifically, the method may link a strong heterologous promoter, instead of the original promoter, but is not limited thereto.

Examples of the known strong promoter may include a cj7 promoter (Korean Patent No. 10-0620092), a cj1 promoter (Korean Patent No. 10-0620092), a lac promoter, a Trp promoter, a trc promoter, a tac promoter, a lambda phage PR promoter, a PL promoter, and a tet promoter, but are not limited thereto.

3) The method of modifying a nucleotide sequence of an initiation codon or 5'-UTR region of the protein may be performed by way of any method known in the art, for example, by replacing the endogenous initiation codon of the protein with another initiation codon having a higher protein expression rate than the endogenous initiation codon, but is not limited thereto.

4) The method of modifying a polynucleotide sequence on a chromosome to enhance the activity of the protein may be performed by way of any method known in the art, for example, by inducing a variation in the expression regulatory sequence via deletion, insertion, non-conservative or conservative substitution, or any combination thereof so as to further enhance the activity of the polynucleotide sequence; or by replacing the sequence with a polynucleotide sequence which is improved to have a stronger activity. The replacement may specifically be insertion of the gene into the chromosome by homologous recombination, but is not limited thereto.

The vector used herein may further include a selection marker to confirm chromosomal insertion. The selection marker is to select cells that are transformed by the vector, that is, to confirm whether or not a desired gene is inserted. Markers providing selectable phenotypes, such as drug resistance, auxotrophy, resistance to cytotoxic agents, or surface protein expression, may be used, but are not limited thereto. Only cells expressing the selection marker are able to survive or to show different phenotypes under an environment treated with a selective agent, and thus the transformed cells may be selected.

5) The method of introducing a foreign polynucleotide having the activity of the protein may be performed by way of any method known in the art, for example, by introducing a foreign polynucleotide encoding a protein having activity identical/similar to that of the protein, or by introducing a codon-optimized variant polynucleotide thereof into the host cell. The foreign polynucleotide may be any polynucleotide without limitation in terms of the origin or sequence thereof, as long as it has activity identical/similar to that of the protein. In addition, an optimized codon thereof may be introduced into the host cell to perform optimized transcription and translation of the introduced foreign polynucleotide in the host cell. The introduction may be performed by any known transformation method suitably selected by those of ordinary skill in the art. When the introduced polynucleotide is expressed in the host cell, the protein is produced, and the activity thereof may be increased.

Lastly, 6) a combination of the methods may be performed by applying any one method of 1) to 5) in combination.

The enhancement of the protein activity may mean that the activity or concentration of the corresponding protein is increased, or the amount of a product produced from the corresponding protein is increased, based on the activity or concentration of the protein expressed in a wild-type or a microorganism before modification, but is not limited thereto. As used herein, the term "strain before modification" or "microorganism before modification" does not exclude a strain including a mutation which may naturally occur in a microorganism, and may refer to a native strain itself, or a strain before trait change due to a genetic modification caused by natural or artificial factors. In the present disclosure, the trait change may be activity enhancement of the phosphate importer. The "strain before modification" or the "microorganism before modification" may be used interchangeably with a "non-variant strain", a "non-modified strain", a "non-variant microorganism", a "non-modified microorganism", or a "reference microorganism".

In the present disclosure, the reference microorganism may be a wild-type microorganism known to produce a purine nucleotide, for example, *Corynebacterium stationis* ATCC6872. Alternatively, the reference microorganism may be a microorganism known to produce a purine nucleotide, for example, CJX1664 (KCCM12285P, Korean Patent No. 10-1950141), CJX1665 (CJX1664::purA(G85S), KCCM12286P, Korean Patent No. 10-1950141), and CJI2335 (KCCM12278P, Korean Patent No. 10-1956510), but is not limited thereto.

As used herein, the term "microorganism producing a purine nucleotide" refers to a microorganism which is prepared by providing a purine nucleotide producing ability for a microorganism having a naturally weak purine nucleotide producing ability or a parent strain having no purine nucleotide producing ability, due to natural or artificial genetic modification. When the microorganism is cultured in a medium, the purine nucleotide may be produced and accumulated in the microorganism, or may be secreted into or accumulated in the medium. The purine nucleotide producing ability may be the trait possessed by the wild-type microorganism of the genus *Corynebacterium*, or may be provided or enhanced by genetic improvement. In the present disclosure, the "microorganism producing a purine nucleotide" may be used interchangeably with a "microorganism having a purine nucleotide producing ability" or a "purine nucleotide-producing strain".

With respect to the objects of the present disclosure, the microorganism producing a purine nucleotide may include any one or more of the polypeptide exhibiting the phosphate importer activity of the present disclosure, the polynucleotide encoding the same, and a vector including the same, and may have increased purine nucleotide productivity, as compared with the wild-type or the microorganism before modification, as the activity of the polypeptide is enhanced by way of the above-described method of enhancing the protein activity, as compared with the endogenous activity. This is significant in that the wild-type microorganism is unable to produce a purine nucleotide or is able to produce a very trace amount thereof even though it produces the purine nucleotide, whereas the microorganism of the present disclosure may have the increased purine nucleotide productivity by introduction of the polypeptide exhibiting the phosphate importer activity of the present disclosure and enhancement of activity thereof.

The phosphate importer may be specifically any one or more selected from the group consisting of PstS, PstC, PstA, and PstB, and more specifically, any one or more selected from PstS, PstC, and a combination of PstS and PstC, but is not limited thereto.

The microorganism producing a purine nucleotide of the present disclosure is not particularly limited, as long as it is able to produce the purine nucleotide, and it may be a microorganism of the genus *Corynebacterium*. The microorganism of the genus *Corynebacterium* may include *Corynebacterium thermoaminogenes*, *Corynebacterium glutamicum*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, *Corynebacterium flavescens*, *Brevibacterium flavum*, *Brevibacterium lactofermentum*, and strains prepared by using the above strains as a parent strain, for example, *Corynebacterium stationis* KCCM12285P and KCCM12286P (Korean Patent No. 10-1950141), *Corynebacterium stationis* KCCM12278P (Korean Patent No. 10-1956510), *Corynebacterium stationis* KCCM12280P (Korean Patent No. 10-1950141), but is not limited thereto. Specifically, the microorganism may be *Corynebacterium stationis* or *Corynebacterium glutamicum*. The microorganism producing a purine nucleotide may mean a microorganism producing a large amount of the purine nucleotide by including a natural or artificial genetic modification, as compared with the wild-type microorganism, e.g., ATCC6872, but is not limited thereto.

As used herein, the term "purine nucleotide" may be specifically any one or more nucleotides selected from the group consisting of 5'-inosine monophosphate (hereinafter referred to as IMP), 5'-xanthosine monophosphate (hereinafter referred to as XMP), and 5'-guanosine monophosphate (hereinafter referred to as GMP). The IMP is a deaminated adenine compound, and refers to a nucleotide composed of one molecule each of hypoxanthine, ribose, and phosphate. The IMP may be biosynthesized from 5'-phosphoribosyl-1-pyrophosphate (PRPP), and specifically, it may be formed by substituting a pyrophosphate group bound to the 1' carbon of PRPP with a nitrogen atom and by constituting an imidazole ring and a pyrimidine ring via nine stages. The XMP refers to a nucleotide resulting from dehydrogenation of IMP, and may be synthesized from IMP by inosine-5'-monophosphate dehydrogenase. The GMP refers to a nucleotide having a structure in which a phosphate group forms an ester bond in a ribose of a guanosine molecule. The GMP may be synthesized by adding ammonia molecules to XMP via 5'-guanylic acid biosynthase (GMP synthase). A method of preparing GMP from XMP and/or a means used in the method may be selected from known techniques.

Another aspect of the present disclosure provides a method of producing a purine nucleotide, the method including the step of culturing, in a medium, the microorganism of the genus *Corynebacterium* producing the purine nucleotide, in which activity of a phosphate importer is enhanced.

The phosphate importer, the microorganism, and the purine nucleotide are the same as described above.

As used herein, the term "culturing" means that the microorganism is grown under appropriately controlled environmental conditions. The culturing process of the present disclosure may be achieved according to an appropriate medium and culture conditions known in the art. Such a culturing process may be used by easy adjustment of the conditions by those skilled in the art according to the strain being selected. Specifically, the culturing may be performed in a batch process, a continuous process, or a fed-batch process, but is not limited thereto.

As used herein, the term "medium" refers to a mixture of nutrients required for culturing the microorganism as main components, and provides nutritional and growth factors as well as water necessary for survival and growth. Specifically, the medium and other culture conditions used in culturing the microorganism of the present disclosure are not particularly limited, as long as the medium is a medium commonly used in culturing microorganisms, but the microorganism of the present disclosure may be cultured in a common medium containing appropriate carbon sources, nitrogen sources, phosphorous sources, inorganic compounds, amino acids and/or vitamins, etc. under aerobic conditions while adjusting temperature, pH, etc.

In the present disclosure, the carbon sources may include carbohydrates such as glucose, fructose, sucrose, maltose, etc.; sugar alcohols such as mannitol, sorbitol, etc.; organic acids such as pyruvic acid, lactic acid, citric acid, etc.; and amino acids such as glutamic acid, methionine, lysine, etc. In addition, natural organic nutrient sources such as starch hydrolysates, molasses, blackstrap molasses, rice bran, cassava, bagasse, and corn steep liquor may be used. Specifically, carbohydrates such as glucose, sterile pretreated molasses (i.e., molasses converted to reduced sugars), etc. may be used, and suitable amounts of other carbon sources may be used without limitation. These carbon sources may be used alone or in a combination of two or more thereof, but are not limited thereto.

The nitrogen sources may include inorganic nitrogen sources such as ammonia, ammonium sulfate, ammonium chloride, ammonium acetate, ammonium phosphate, ammonium carbonate, ammonium nitrate, etc.; amino acids such as glutamic acid, methionine, glutamine, etc.; and organic nitrogen sources such as peptone, NZ-amine, meat extract, yeast extract, malt extract, corn steep liquor, casein hydrolysate, fish meal or digested products thereof, defatted soybean cake or digested products thereof, etc. These nitrogen sources may be used alone or in a combination of two or more thereof, but are not limited thereto.

The phosphorus sources may include potassium phosphate monobasic, potassium phosphate dibasic, and corresponding sodium-containing salts. Inorganic compounds may include sodium chloride, calcium chloride, iron chloride, magnesium sulfate, iron sulfate, manganese sulfate, calcium carbonate, etc. In addition, amino acids, vitamins, and/or appropriate precursors may be included. These components or precursors may be added to the medium in a batch or continuous manner, but are not limited thereto.

In the present disclosure, pH of the medium may be adjusted by adding compounds, such as ammonium hydroxide, potassium hydroxide, ammonia, phosphoric acid, sulfuric acid, etc., to the medium in an appropriate manner during the culturing of the microorganism. Further, an antifoaming agent, such as fatty acid polyglycol ester, may be used to prevent foam generation during culturing. Further, the aerobic conditions of the medium may be maintained by introducing oxygen or an oxygen-containing gas mixture into the medium, or the anaerobic and microaerobic states may be maintained without the injection of a gas or by introducing nitrogen, hydrogen, or carbon dioxide gas, but are not limited thereto.

The temperature of the medium may be 20° C. to 50° C., and specifically 30° C. to 37° C., but is not limited thereto. The culturing may be continued until the production of the useful product reaches a desired level. Specifically, the culturing may be continued for 10 hours to 100 hours, but is not limited thereto.

The purine nucleotide produced by the culturing may be discharged into the medium or may not be discharged and may remain in the cell.

The method may include the step of adding an enzyme to the medium or the step of adding a microorganism expressing the enzyme. For example, the method may further include the step of adding an enzyme that converts XMP into GMP or the step of adding a microorganism expressing the enzyme, and/or the step of culturing the microorganism, after the step of culturing the microorganism producing XMP.

The method may include the step of recovering the purine nucleotide from the cultured medium or the microorganism.

The method of recovering the purine nucleotide produced in the culturing step of the present disclosure may be collecting the purine nucleotide from the culture broth using an appropriate method known in the art according to the culturing method. For example, centrifugation, filtration, anion-exchange chromatography, crystallization, HPLC, etc. may be used, and the purine nucleotide may be recovered from the medium or the microorganism using an appropriate method known in the art. The culture broth may also be called a fermentation broth.

Further, the recovering step may include a purification process, and may be performed using an appropriate method known in the art. Therefore, the collected purine nucleotide may be in a pure form, or may be a microbial fermentation broth containing the purine nucleotide (*Introduction to Biotechnology and Genetic Engineering*, A. J. Nair., 2008).

Still another aspect of the present disclosure provides a composition for producing a purine nucleotide, the composition including the microorganism of the genus *Corynebacterium*, in which activity of a phosphate importer is enhanced.

The phosphate importer, the microorganism, and the purine nucleotide are the same as described above.

The composition for producing a purine nucleotide may include a composition capable of enhancing activities of proteins without limitation, wherein the proteins are encoded by any one or more genes selected from the group consisting of pstS, pstC, pstA, and pstB, which are phosphate importer systems encoded by pstSCAB operon, as the phosphate importer, and descriptions thereof are the same as described above.

Hereinafter, the present disclosure will be described in more detail with reference to Examples. However, these Examples are only for illustrating the present disclosure, and it is apparent to those skilled in the art to which the present disclosure pertains that the scope of the present disclosure is not intended to be limited by these Examples.

Example 1: Preparation of pstS Initiation Codon-Altered Strain and Evaluation of XMP Productivity 1-1. Preparation of Recombinant Vector for pstS Initiation Codon Alteration and XMP-Producing Strain To prepare strains by enhancing activity of endogenous pstS gene in CJX1664, which is an XMP-producing strain (*Corynebacterium stationis* ATCC6872-derived XMP-producing strain, KCCM12285P, Korean Patent No. 10-1950141), and CJX1664::purA(G85S), which is a purA (G85S) variant strain thereof (KCCM12286P, Korean Patent No. 10-1950141), an experiment was performed to replace GTG, which is an endogenous initiation codon of pstS, with ATG, which is an initiation codon showing a higher protein expression rate.

A chromosomal gene of ATCC6872 strain, which is a wild-type *Corynebacterium stationis*, was isolated using a G-spin total DNA extraction mini kit (Cat. No. 17045, Intron) according to a protocol provided in the kit, and polymerase chain reaction was performed using a pair of primers of SEQ ID NO: 9 and SEQ ID NO: 10 and a pair of primers of SEQ ID NO: 11 and SEQ ID NO: 12 to obtain a pair of gene fragments (pstS(ATG)-A and pstS(ATG)-B), respectively. PCR was performed as follows: denaturation at 94° C. for 5 minutes, followed by denaturation at 94° C. for 30 seconds, annealing at 55° C. for 30 seconds, and 20 cycles of polymerization at 72° C. for 1 minute, and polymerization at 72° C. for 7 minutes. As a result, a polynucleotide of 769 bp and a polynucleotide of 766 bp were obtained.

Secondary PCR was performed using the two fragments as a template to obtain a polynucleotide template of 1.5 kbp. The obtained gene fragment was digested with a restriction enzyme XbaI (New England Biolabs, Beverly, MA). Thereafter, T4 ligase (New England Biolabs, Beverly, MA) was used to ligate the gene fragment and a linear pDZ vector which had been digested with XbaI restriction enzyme. The prepared vector was designated as pDZ-pstS(ATG).

The pDZ-pstS(ATG) vector was transformed into each of the XMP-producing CJX1664 and CJX1664::purA(G85S) by electroporation, and then strains in which both the variant gene and the vector were inserted into the chromosome were selected as a primary candidate on a selection medium containing 25 mg/L kanamycin. Thereafter, an endogenous initiation codon of pstS on the chromosome was altered into ATG through a secondary crossover process using homology between the gene existing on the chromosome and the gene being inserted through the vector. A final strain was obtained from which the vector containing a kanamycin resistance gene was removed. The gene in which the initiation codon was altered was primarily examined through mismatch PCR using primers of SEQ ID NO: 13 and SEQ ID NO: 12, and SEQ ID NO: 14 and SEQ ID NO: 12, and was finally confirmed through sequencing. The pstS initiation codon-altered strains obtained by the above method were designated as CJX1664_pstS(g1a) and CJX1664::purA(G85S)_pstS(g1a).

Sequences of the primers used above are as follows.

TABLE 1

| SEQ ID NO: | Name | Sequence |
|---|---|---|
| 9 | pstS(ATG)-A-F | GGGTCTAGACCACAAACAGAATTAATGGTA |
| 10 | pstS(ATG)-A-R | GCTTAAAGTTGCGAATCATGGGGAAAC |
| 11 | pstS(ATG)-B-F | CCGGAAAGGTTTCCCCATGATTCGCAA |
| 12 | pstS(ATG)-B-R | GGGTCTAGAGACGTAGGTGATGCCACCGTT |
| 13 | pstS(ATG)-mismatch-wt-F | GAAAGGTTTCCCCG |
| 14 | pstS (ATG)-mismatch-mut-F | GAAAGGTTTCCCCA |

1-2. Evaluation of XMP Productivity of pstS Initiation Codon-Altered Strain

To measure XMP productivity of the prepared strains, a flask test was performed. Each of CJX1664, CJX1664_pstS (g1a), CJX1664::purA(G85S), and CJX1664::purA(G85S)_pstS(g1a) was seeded in a 14 mL tube containing 2.5 mL of the following seed medium, and cultured with shaking at 30° C. and 170 rpm for 24 hours. 0.7 mL of the seed culture broth was seeded in a 250 mL corner-baffle flask containing 32 mL (24 mL of main medium+8 mL of separate sterile medium) of the following production medium, and cultured with shaking at 30° C. and 170 rpm for 75 hours.

Compositions of the seed medium, the main medium, and the separate sterile medium are as follows.

XMP Flask Seed Medium 30 g/L glucose, 15 g/L peptone, 15 g/L yeast extract, 2.5 g/L sodium chloride, 3 g/L urea, 150 mg/L adenine, 150 mg/L guanine, pH 7.0 (based on 1 L of medium)

XMP Flask Production Medium (Main Medium)

50 g/L glucose, 10 g/L magnesium sulfate, 100 mg/L calcium chloride, 20 mg/L iron sulfate, 10 mg/L manganese sulfate, 10 mg/L zinc sulfate, 0.8 mg/L copper sulfate, 20 mg/L histidine, 15 mg/L cysteine, 15 mg/L beta-alanine, 100 μg/L biotin, 5 mg/L thiamine, 50 mg/L adenine, 25 mg/L guanine, 15 mg/L niacin, pH 7.0 (based on 1 L of medium)

XMP Flask Production Medium (Separate Sterile Medium)

18 g/L potassium phosphate monobasic, 42 g/L potassium phosphate dibasic, 7 g/L urea, 5 g/L ammonium sulfate (based on 1 L of medium)

The results of measuring XMP production by way of a method using HPLC after terminating the culturing are as in Table 2 below.

TABLE 2

| | Strain | XMP (g/L) | | | |
|---|---|---|---|---|---|
| | | Flask 1 | Flask 2 | Flask 3 | Mean |
| Control group 1 | CJX1664 | 2.1 | 2.2 | 2.1 | 2.1 |
| Experimental group 1 | CJX1664_pstS(g1a) | 2.5 | 2.5 | 2.6 | 2.5 |

TABLE 2-continued

|  |  | XMP (g/L) | | | |
| --- | --- | --- | --- | --- | --- |
| Strain | | Flask 1 | Flask 2 | Flask 3 | Mean |
| Control group 2 | CJX1664::purA(G85S) | 2.2 | 2.2 | 2.3 | 2.2 |
| Experimental group 2 | CJX1664::purA(G85S)_pstS(g1a) | 2.5 | 2.6 | 2.6 | 2.6 |

As shown in Table 2, CJX1664_pstS(g1a) and CJX1664::purA(G85S)_pstS(g1a), in which the initiation codon of pstS was replaced, showed 19% and 15% increases in the XMP concentration, as compared with the parent strains thereof, CJX1664 and CJX1664::purA(G85S), respectively.

These results indicate that alteration of initiation codon of pstS in the XMP-producing strain of the genus *Corynebacterium* is effective in the XMP production.

Example 2: Preparation of pstC Initiation Codon-Altered Strain and Evaluation of IMP Productivity 2-1. Preparation of Recombinant Vector for pstC Initiation Codon Alteration and IMP-Producing Strain A chromosomal gene of CJI2335, which is an IMP-producing strain (*Corynebacterium stationis* ATCC6872-derived IMP-producing strain, KCCM12278P, Korean Patent No. 10-1956510), was isolated, and polymerase chain reaction was performed using a pair of primers of SEQ ID NO: 15 and SEQ ID NO: 16 and a pair of primers of SEQ ID NO: 17 and SEQ ID NO: 18 to obtain gene fragments (pstC(ATG)-A and pstC(ATG)-B), respectively. PCR was performed as follows: denaturation at 94° C. for 5 minutes, followed by denaturation at 94° C. for 30 seconds, annealing at 55° C. for 30 seconds, and 20 cycles of polymerization at 72° C. for 1 minute, and polymerization at 72° C. for 7 minutes. As a result, a polynucleotide of 771 bp and a polynucleotide of 766 bp were obtained.

Secondary PCR was performed using the two fragments as a template to obtain a polynucleotide template of 1.5 kbp. The obtained gene fragment was digested with XbaI restriction enzyme. Thereafter, T4 ligase was used to ligate the gene fragment and a linear pDZ vector which had been digested with XbaI restriction enzyme. The prepared vector was designated as pDZ-pstC(ATG).

The pDZ-pstC(ATG) vector was transformed into the IMP-producing CJI2335 and CJI2332::purA(G85S) (purA (G85S) variant strain of *Corynebacterium stationis* ATCC6872-derived IMP-producing strain, KCCM12280P, Korean Patent No. 10-1950141) by electroporation, and then strains in which the variant gene was inserted into the chromosome were selected as a primary candidate on a selection medium containing 25 mg/L kanamycin. Thereafter, a secondary crossover process was performed in the same manner as in Example 1 to obtain a strain in which an endogenous initiation codon of pstC on the chromosome was altered into ATG. The gene in which the initiation codon was altered was primarily examined through mismatch PCR using primers of SEQ ID NO: 19 and SEQ ID NO: 18, and SEQ ID NO: 20 and SEQ ID NO: 18, and was finally confirmed through sequencing. The pstC initiation codon-altered strains obtained by the above method were designated as CJI2335_pstC(g1a) and CJI2332::purA(G85S)_pstC(g1a).

Sequences of the primers used above are as follows.

TABLE 3

| SEQ ID NO: | Name | Sequence |
| --- | --- | --- |
| 15 | pstC(ATG)-A-F | GGGTCTAGACATCAACCTGAGCACCGAAAC |
| 16 | pstC(ATG)-A-R | TCAGGAGTGTCGTAAACATACCATACA |
| 17 | pstC(ATG)-B-F | CGCTGGCTTGTATGGTATGTTTACGAC |
| 18 | pstC(ATG)-B-R | GGGTCTAGAACCGGTAAACAGGTTACGGCC |
| 19 | pstC(ATG)-mismatch-wt-F | TGGCTTGTATGGTG |
| 20 | pstC(ATG)-mismatch-mut-F | TGGCTTGTATGGTA |

2-2. Evaluation of IMP Productivity of pstC Initiation Codon-Altered Strain

To Examine improvement in the IMP productivity of CJI2335_pstC(g1a) and CJI2332::purA(G85S)_pstC(g1a) which are the pstC initiation codon-altered strains prepared in Example 2-1, the following experiment was performed.

The strain was seeded in 5 mL of a seed medium in an autoclaved test tube having a diameter of 18 mm, and cultured with shaking at a temperature of 30° C. for 24 hours, and used as a seed culture broth. 29 mL of a fermentation medium was dispensed in a 250 mL shaking Erlenmeyer flask, and then autoclaved at a temperature of 121° C. for 15 minutes. 2 mL of the seed culture broth was seeded therein and cultured for 3 days. The culture conditions were controlled at 170 rpm, 30° C., and pH 7.8.

Compositions of the seed medium and the fermentation medium are as follows.

IMP Seed Medium
1% glucose, 1% peptone, 1% meat extract, 1% yeast extract, 0.25% sodium chloride, 100 mg/L adenine, 100 mg/L guanine, pH 7.2 (based on 1 L of medium)

IMP Flask Fermentation Medium
0.1% sodium glutamate, 1% ammonium chloride, 1.2% magnesium sulfate, 0.01% calcium chloride, 20 mg/L iron sulfate, 20 mg/L manganese sulfate, 20 mg/L zinc sulfate, 5 mg/L copper sulfate, 23 mg/L L-cysteine, 24 mg/L alanine, 8 mg/L nicotinic acid, 45 µg/L biotin, 5 mg/L thiamine-HCl, 30 mg/L adenine, 1.9% phosphoric acid (85%), 4.2% glucose, 2.4% raw sugar (based on 1 L of medium)

After terminating the culturing, IMP production was measured by way of a method using HPLC. The results of culturing CJI2335_pstC(g1a) and CJI2332::purA(G85S)_pstC(g1a) are as in Table 4 below.

TABLE 4

| Strain | | IMP (g/L) | | | |
|---|---|---|---|---|---|
| | | Flask 1 | Flask 2 | Flask 3 | Mean |
| Control group 1 | CJI2335 | 0.7 | 0.6 | 0.6 | 1.0 |
| Experimental group 1 | CJI2335_pstC(g1a) | 0.8 | 0.8 | 0.7 | 0.8 |
| Control group 2 | CJI2332::purA(G85S) | 0.6 | 0.6 | 0.6 | 0.6 |
| Experimental group 2 | CJI2332::purA(G85S)_pstC(g1a) | 0.8 | 0.7 | 0.7 | 0.7 |

As shown in Table 4, when IMP accumulation in the medium was compared with CJI2335 and CJI2332::purA (G85S), which are parent strains, CJI2335_pstC(g1a) and CJI2332::purA(G85S)_pstC(g1a) showed 21% and 22% increases in the yield, as compared with the parent strains thereof, under the same conditions.

Example 3: Preparation of pstC Initiation Codon-Altered Strain and Evaluation of XMP Productivity 3-1. Preparation of Recombinant Vector for pstC Initiation Codon Alteration and XMP-Producing Strain The pDZ-pstC(ATG) vector prepared in Example 2-1 was transformed into each of CJX1664 and CJX1664::purA (G85S) strains having XMP productivity by electroporation, and then strains in which the variant gene was inserted into the chromosome were selected as a primary candidate on a selection medium containing 25 mg/L kanamycin. Thereafter, a secondary crossover process was performed to obtain a strain in which an endogenous initiation codon of pstC on the chromosome was altered into ATG. The gene in which the initiation codon was altered was examined in the same manner as in Example 2-1. The pstC initiation codon-altered strains obtained by the above method were designated as CJX1664_pstC(g1a) and CJX1664::purA(G85S)_pstC (g1a), respectively.

3-2. Evaluation of XMP Productivity of pstC Initiation Codon-Altered Strain

To examine the XMP productivity of CJX1664_pstC(g1a) and CJX1664::purA(G85S)_pstC(g1a) strains, a flask test was performed in the same manner as in Example 1-2, and the results of culturing are shown in Table 5 below.

As shown in Table 5, CJX1664_pstC(g1a) and CJX1664:: purA(G85S)_pstC(g1a) showed 8% and 10% improvements in the XMP yield, as compared with the parent strains, respectively.

Example 4: Preparation of pstS and pstC Initiation Codon Co-Altered Strain and Evaluation of IMP Productivity 4-1. Preparation of IMP-Producing pstS and pstC Initiation Codon Co-Altered Strain To prepare a strain in which the initiation codon (ATG) showing high activity was introduced into both pstS and pstC genes, the pDZ-pstS(ATG) vector prepared in the same manner as in Example 1-1 was introduced into CJI2335_pstC(g1a) and CJI2332::purA(G85S)_pstC(g1a) strains prepared in Example 2-1, respectively. The vector-introduced strains were selected in the same manner as in Example 1-1. Through this procedure, strains which were transformed with the recombinant vector having the altered initiation codons of pstS and pstC were selected, and the preparation of the strains was completed through secondary selection. The prepared strains were designated as CJI2335_pstS (g1a)_ pstC(g1a) and CJI2332::purA(G85S)_ pstS(g1a)_pstC(g1a), respectively.

4-2. Evaluation of IMP Productivity of pstS and pstC Initiation Codon Co-Altered Strain To examine the IMP productivity of CJI2335_pstS(g1a)_pstC(g1a) and CJI2332::purA(G85S)_pstS(g1a)_pstC(g1a) strains, a flask test was performed in the same manner as in Example 2-2.

After terminating the culturing, IMP production was measured by way of a method using HPLC. The results of culturing CJI2335_pstS(g1a)_pstC(g1a) and CJI2332::purA (G85S)_pstS(g1a)_pstC(g1a) are as in Table 6 below.

TABLE 5

| Strain | | XMP (g/L) | | | |
|---|---|---|---|---|---|
| | | Flask 1 | Flask 2 | Flask 3 | Mean |
| Control group 1 | CJX1664 | 2.1 | 2.2 | 2.1 | 2.1 |
| Experimental group 1 | CJX1664_pstC(g1a) | 2.3 | 2.3 | 2.3 | 2.3 |
| Control group 2 | CJX1664::purA(G85S) | 2.2 | 2.2 | 2.3 | 2.2 |
| Experimental group 2 | CJX1664::purA(G85S)_pstC(g1a) | 2.5 | 2.5 | 2.4 | 2.5 |

TABLE 6

|  | | IMP (g/L) | | | |
| --- | --- | --- | --- | --- | --- |
|  | Strain | Flask 1 | Flask 2 | Flask 3 | Mean |
| Control group 1 | CJI2335_pstC(g1a) | 0.8 | 0.8 | 0.7 | 0.8 |
| Experimental group 1 | CJI2335_pstS(g1a)_pstC(g1a) | 0.9 | 0.9 | 0.8 | 0.9 |
| Control group 2 | CJI2332::purA(G85S)_pstC(g1a) | 0.8 | 0.7 | 0.7 | 0.7 |
| Experimental group 2 | CJI2332::purA(G85S)_pstS(g1a)_pstC(g1a) | 0.9 | 0.8 | 0.9 | 0.9 |

As shown in Table 6, CJI2335_pstS(g1a)_pstC(g1a) and CJI2332::purA(G85S)_pstS(g1a)_pstC(g1a) showed 13% and 18% improvements in the IMP production, as compared with the parent strains, respectively.

Example 5: Preparation and Evaluation of pstSCAB Operon-Enhanced IMP-Producing Strain for pstSC Enhancement 5-1. Preparation of Vector Having Increased Copy Number of pstSCAB Operon for Enhancement of *Corynebacterium stationis*-Derived pstSC and Preparation of IMP-Producing Strain A microorganism was prepared in which the copy number was increased for enhancement of pstSC activity, and IMP productivity was evaluated.

The chromosome of the wild-type *Corynebacterium stationis* ATCC6872 strain was isolated using the same kit as in Example 1, and PCR was performed using the chromosome as a template. As a polymerase, Maxime PCR PreMix (i-pfu) high-fidelity DNA polymerase (Intron) was used, and PCR was performed as follows: denaturation at 95° C. for 5 minutes, followed by denaturation at 95° C. for 30 seconds, annealing at 54° C. for 30 seconds, and 24 cycles of polymerization at 72° C. for 9 minutes and 30 seconds. As a result, a pair of pstSCAB genes including the promoter region (pstSCAB-A and pstSCAB-B) was obtained. pstSCAB-A had a size of 4960 bp and was amplified using primers of SEQ ID NO: 21 and SEQ ID NO: 22, and pstSCAB-B had a size of 4960 bp and was amplified using primers of SEQ ID NO: 21 and SEQ ID NO: 23. The gene fragments were cloned through three-fragment ligation into a pDZ vector which was linearized by treatment with XbaI and SpeI restriction enzymes (pstSCAB-A: XbaI, pstSCAB-B: XbaI and SpeI), of which sites were included at each end of pstSCAB-A and pstSCAB-B. Finally, a pDZ-2pstSCAB recombinant vector was prepared, in which two pstSCAB genes were consecutively cloned.

The pDZ-2pstSCAB vector was transformed into each of the IMP-producing strains, CJI2335 and CJI2332::purA (G85S), by electroporation. Strains, each having a total of two pstSCAB genes, in which one pstSCAB gene was additionally inserted next to the endogenous pstSCAB gene on the chromosome, were obtained by a secondary crossover process. The consecutively inserted pstSCAB genes were finally confirmed by PCR using primers of SEQ ID NO: 24 and SEQ ID NO: 25 capable of amplifying the linkage site of two pstSCAB genes. Through this procedure, strains transformed with the vector having the increased copy number of pstSCAB operon were selected, and the prepared strains were designated as CJI2335_2pstSCAB and CJI2332::purA(G85S)_2pstSCAB, respectively.

Sequences of the primers used above are as follows.

TABLE 7

| SEQ ID NO: | Name | Sequence |
| --- | --- | --- |
| 21 | pstSCAB-Xba-F | TGCTCTAGAGAAGTGGCACGATGAAGTATCGCC |
| 22 | pstSCAB XbaI-R | TGCTCTAGAGCAGTCGATATTGCGCTGCTATCAC |
| 23 | pstSCAB SpeI-R | ACGACTAGTGCAGTCGATATTGCGCTGCTATCAC |
| 24 | pstSCAB-2copy-check-F | CACCATCGTGATCGTTACCCACAA |
| 25 | pstSCAB-2copy-check-R | GAATCATCTGCGGAATCAGAGCAAG |

5-2. Evaluation of IMP Productivity of Strain Having Increased Copy Number of *Corynebacterium stationis*-Derived pstSCAB Operon IMP productivity was evaluated using CJI2335_2pstSCAB and CJI2332::purA(G85S)_2pstSCAB strains which had the increased copy number of *Corynebacterium stationis*-derived pstSC to have the enhanced activity, and their parent strains CJI2335 and CJI2332::purA(G85S) by way of the flask test of Example 2-2, and the results are shown in Table 8 below.

TABLE 8

|  | Strain | IMP (g/L) | | | |
| --- | --- | --- | --- | --- | --- |
|  |  | Flask 1 | Flask 2 | Flask 3 | Mean |
| Control group 1 | CJI2335 | 0.7 | 0.6 | 0.6 | 0.6 |
| Experimental group 1 | CJI2335_2pstSCAB | 0.8 | 0.8 | 0.8 | 0.8 |
| Control group 2 | CJI2332::purA(G85S) | 0.6 | 0.6 | 0.6 | 0.6 |
| Experimental group 2 | CJI2332::purA(G85S)_2pstSCAB | 0.8 | 0.7 | 0.8 | 0.8 |

As shown in Table 8, the above results of the flask fermentation test showed that CJI2335_2pstSCAB and CJI2332::purA(G85S)_2pstSCAB showed 26% and 27% improvements in the IMP productivity, as compared with the parent strains, respectively.

Example 6: Preparation and Evaluation of pstSCAB Operon-Enhanced XMP-Producing Strain for pstSC Enhancement 6-1. Preparation of XMP-Producing Strain Having Increased Copy Number of Corynebacterium stationis-Derived pstS-CAB Operon The pDZ-2pstSCAB vector prepared in Example 5-1 was transformed into the XMP-producing strains, CJX1664 and CJX1664::purA(G85S), by electroporation, and strains having a total of two pstSCAB genes, in which one pstSCAB gene was additionally inserted next to the endogenous pstSCAB gene on the chromosome, were obtained by a secondary crossover process. The consecutively inserted pstSCAB genes were finally confirmed by PCR using primers of SEQ ID NO: 24 and SEQ ID NO: 25 capable of amplifying the linkage site of two pstSCAB genes. The strains having the increased copy number of pstSCAB which were obtained by the above method were designated as CJX1664_2pstSCAB and CJX1664::purA(G85S)_2pstSCAB, respectively.

6-2. Evaluation of XMP Productivity of Strain Having Increased Copy Number of Corynebacterium stationis-Derived pstSCAB Operon To measure XMP productivity of CJX1664_2pstSCAB and CJX1664::purA(G85S)_2pstSCAB strains, a flask test was performed in the same manner as in Example 1-2.

After terminating the culturing, XMP production was measured by way of a method using HPLC. The results of culturing CJX1664, CJX1664::purA(G85S), CJX1664_2pstSCAB, and CJX1664::purA(G85S)_2pstSCAB are as in Table 9 below.

Example 7: Preparation and Evaluation of pstSCAB Promoter-Substituted IMP-Producing Strain for pstSC Enhancement 7-1. Preparation of Recombinant Vector for pstSCAB Promoter Substitution and Preparation of IMP-Producing Strain To increase an expression level of pstSC encoding a component protein of the phosphate importer Pst system, the pstS promoter itself in the chromosome was substituted with cj7 promoter, which is known to have strong activity (Korean Patent No. 10-0620092).

First, a homologous recombination vector including the cj7 promoter and having the original sequence on the chromosome at both ends of the promoter was prepared.

In detail, to prepare a vector for insertion of the cj7 promoter into the pstS gene, the chromosome of the wild-type Corynebacterium stationis ATCC6872 strain was isolated by way of the method of Example 1, and PCR was performed using the chromosome as a template and Maxime PCR premix (i-pfu) high-fidelity DNA polymerase (Intron). PCR was performed as follows: denaturation at 95° C. for 5 minutes, followed by denaturation at 95° C. for 30 seconds, annealing at 54° C. for 30 seconds, and 24 cycles of polymerization at 72° C. for 1 minute and 30 seconds. As a result, two different kinds of PCR products (PstSpro-A and PstSpro-B) were obtained. PstSpro-A had a size of 981 bp, and was amplified using SEQ ID NO: 26 and SEQ ID NO: 27 as primers. PstSpro-B had a size of 2026 bp, and was amplified using SEQ ID NO: 28 and SEQ ID NO: 29 as primers. Secondary PCR was performed using the two kinds of amplification products as templates by a sewing PCR technique. PCR was performed under the same conditions as above, and a PCR product of the pstS gene of 2988 bp including the BamHI and NdeI restriction sites in the middle thereof was obtained. Thereafter, the amplification product was digested using the restriction sites (PstSpro-A and PstSpro-B: XbaI) at both ends thereof, and then cloned into the pDZ vector by T4 ligase activity, and as a result, a pDZ-PstSpro vector was obtained.

TABLE 9

|  | Strain | XMP (g/L) | | | |
| --- | --- | --- | --- | --- | --- |
|  |  | Flask 1 | Flask 2 | Flask 3 | Mean |
| Control group 1 | CJX1664 | 2.1 | 2.2 | 2.1 | 2.1 |
| Experimental group 1 | CJX1664_2pstSCAB | 2.3 | 2.3 | 2.4 | 2.3 |
| Control group 2 | CJX1664::purA(G85S) | 2.2 | 2.2 | 2.3 | 2.2 |
| Experimental group 2 | CJX1664::purA(G85S)_2pstSCAB | 2.4 | 2.4 | 2.4 | 2.4 |

As shown in Table 9, CJX1664_2pstSCAB and CJX1664::purA(G85S)_2pstSCAB showed 9% and 7% improvements in the XMP productivity, as compared with the parent strains, respectively.

The obtained vector was used to prepare a vector capable of substituting the cj7 promoter for the promoter of the pstS gene on the chromosome of CJI2335 or CJI2332::purA(G85S).

In detail, the genome of the wild-type *Corynebacterium stationis* ATCC6872 was used as a template to perform PCR as follows. As a polymerase, Maxime PCR PreMix (i-pfu) high-fidelity DNA polymerase (Intron) was used. PCR was performed as follows: denaturation at 95° C. for 5 minutes, followed by denaturation at 95° C. for 30 seconds, annealing at 54° C. for 30 seconds, and 24 cycles of polymerization at 72° C. for 2 minutes and 30 seconds. As a result, a gene having BamHI and NdeI restriction sites at both ends of the cj7 promoter gene was obtained. This gene was amplified using SEQ ID NO: 30 and SEQ ID NO: 31 as primers, and its size was 491 bp. This gene and the pDZ-PstSpro vector were treated with BamHI and NdeI restriction enzymes, and cloned by way of a method using T4 ligase to obtain a pDZ-pCJ7/PstSCAB vector.

The prepared pDZ-pCJ7/PstSCAB vector was transformed into an IMP-producing *Corynebacterium stationis* CN01-1811 strain by electroporation, and through a secondary crossover process, a strain was prepared in which the endogenous pstSCAB promoter on the chromosome was substituted with the cj7 promoter. The cj7 promoter substitution was finally confirmed by PCR using a pair of primers of SEQ ID NO: 32 and SEQ ID NO: 33 capable of linking and amplifying the cj7 promoter and part of the pstS gene. The strains obtained by the above method were designated as CJI2335_Pcj7/pstS and CJI2332::purA(G85S)_Pcj7/pstS, respectively.

Sequences of the primers used above are as follows.

As shown in Table 11, CJI2335_Pcj7/pstS and CJI2332::purA(G85S)_Pcj7/pstS strains, each having the enhanced pstSCAB promoter, showed 21% and 28% improvements in the IMP productivity in the flask fermentation, as compared with the parent strains, respectively.

Example 8: Preparation and Evaluation of pstSCAB Promoter-Substituted XMP-Producing Strain for pstSC Enhancement 8-1. Preparation of pstSCAB Promoter-Substituted XMP-Producing Strain The pDZ-pCJ7/PstSCAB vector prepared in Example 7-1 was transformed into each of XMP-producing CJX1664 and CJX1664::purA(G85S) strains by electroporation. Through a secondary crossover process, strains were prepared in which the endogenous pstSCAB promoter on the chromosome was substituted with the cj7 promoter. The cj7 promoter substitution was finally confirmed by PCR using a pair of primers of SEQ ID NO: 32 and SEQ ID NO: 33 capable of linking and amplifying the cj7 promoter and part of the pstS gene. The strains obtained by way of the above method were designated as CJX1664_Pcj7/pstS and CJX1664::purA(G85S)_Pcj7/pstS, respectively.

TABLE 10

| SEQ ID NO: | Name | Sequence |
|---|---|---|
| 26 | PstSpro-A-F | TGCTCTAGAGAAGCAGTTGCCGCAAGCG |
| 27 | PstS-pro-A-R | CATATGGAATTCCGGATCCGGGGAAACCTTTCCGGTTAATTTCAG |
| 28 | PstSpro-B-F | GGATCCGGAATTCCATATGATTCGCAACTTTAAGCGCTCC |
| 29 | PstSpro-B-R | TGCTCTAGACAGACAGGCCCTCATCCTGG |
| 30 | CJ7pro-F | CGCGGATCCTTCCTTCAGGCTAATCTTTTCCGGG |
| 31 | CJ7pro-R | GGAATTCCATATGCATATGTGTTTCCTTTCGTTGGGTACG |
| 32 | CJ7pro-check-F | CTACGACCTCAGCGTGATTGGTTTG |
| 33 | PstS-check-R | CAGGAAGTCCTTGACCAAGTTTGCC |

7-2. Evaluation of IMP Productivity of Strain Having pstSCAB Promoter Substitution IMP productivity was evaluated using CJI2335_Pcj7/pstS and CJI2332::purA(G85S)_Pcj7/pstS strains which had the enhanced activity by employing the cj7 promoter of *Corynebacterium stationis*-derived pstSC, and their parent strains CJI2335 and CJI2332::purA(G85S) by the flask test of Example 2-2, and the results are shown in Table 11 below.

8-2. Evaluation of XMP Productivity of pstSCAB Promoter-Substituted Strain

XMP productivity was evaluated using CJX1664_Pcj7/pstS and CJX1664::purA(G85S)_Pcj7/pstS strains which had the enhanced activity by employment of the cj7 promoter of *Corynebacterium stationis*-derived pstSC, and parent strains CJX1664 and CJX1664::purA(G85S) by way of the flask test of Example 1-2, and the results are shown in Table 12 below.

TABLE 11

| | Strain | IMP (g/L) | | | |
|---|---|---|---|---|---|
| | | Flask 1 | Flask 2 | Flask 3 | Mean |
| Control group 1 | CJI2335 | 0.7 | 0.6 | 0.6 | 0.6 |
| Experimental group 1 | CJI2335_Pcj7/pstS | 0.8 | 0.8 | 0.7 | 0.8 |
| Control group 2 | CJI2332::purA(G85S) | 0.6 | 0.6 | 0.6 | 0.6 |
| Experimental group 2 | CJI2332::purA(G85S)_Pcj7/pstS | 0.8 | 0.8 | 0.8 | 0.8 |

TABLE 12

| | Strain no. | XMP (g/L) | | | |
| --- | --- | --- | --- | --- | --- |
| | | Flask 1 | Flask 2 | Flask 3 | Mean |
| Control group 1 | CJX1664 | 2.1 | 2.2 | 2.1 | 2.1 |
| Experimental group 1 | CJX1664_Pcj7/pstS | 2.5 | 2.3 | 2.5 | 2.4 |
| Control group 2 | CJX1664::purA(G85S) | 2.2 | 2.2 | 2.3 | 2.2 |
| Experimental group 2 | CJX1664::purA(G85S)_Pcj7/pstS | 2.5 | 2.5 | 2.5 | 2.5 |

As shown in Table 12, CJX1664_Pcj7/pstS and CJX1664::purA(G85S)_Pcj7/pstS strains, each having the enhanced pstSCAB promoter, showed 14% and 12% improvements in the XMP productivity in the flask fermentation, as compared with the parent strains, respectively.

CJX1664_Pcj7/pstS was designated as CJX1911, and CJX1664::purA(G85S)_Pcj7/pstS was designated as CJX1912, and these were deposited under the Budapest Treaty in an international depositary authority, the Korean Culture Center of Microorganisms, on Dec. 20, 2019, with Accession Nos. KCCM12647P and KCCM12648P, respectively.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

EFFECT OF THE INVENTION

Intracellular uptake of phosphate, which is a key component in the production of purine nucleotides, may be improved by enhancing activity of a phosphate importer according to the present disclosure. Therefore, a microorganism producing purine nucleotides may efficiently produce purine nucleotides. In the industrial-scale production of purine nucleotides, the microorganism may greatly contribute to cost reduction.

---

What is claimed is:

1. A method of producing a purine nucleotide, the method comprising:

the step of culturing, in a medium, a microorganism of the genus *Corynebacterium* having an increased purine nucleotide productivity compared to an unmodified microorganism, wherein the microorganism of the genus *Corynebacterium*

(a) is modified such that an activity of a phosphate importer system encoded by pstSCAB operon is enhanced in comparison with an endogenous activity thereof, and (b) is *Corynebacterium stationis*, and the step of recovering the purine nucleotide from the cultured medium or microorganism.

2. The method of claim 1, wherein the purine nucleotide is any one or more selected from the group consisting of 5'-inosine monophosphate, 5'-xanthosine monophosphate, and 5'-guanosine monophosphate.

3. The method of claim 1, wherein the enhancement of the activity of the phosphate importer system is enhancement of activity of proteins encoded by any one or more genes selected from the group consisting of pstS, pstC, pstA, and pstB.

4. The method of claim 3, wherein the protein encoded by the pstS gene includes the amino acid sequence of SEQ ID NO: 1.

5. The method of claim 3, wherein the protein encoded by the pstC gene includes the amino acid sequence of SEQ ID NO: 3.

* * * * *